United States Patent [19]

Lewis

[11] 4,194,622
[45] Mar. 25, 1980

[54] STERILIZABLE PACKAGE AND A METHOD OF PACKAGING FOR STERILIZATION

[75] Inventor: Robert P. Lewis, Oceanport, N.J.

[73] Assignee: Faser Industries, Saddle Brook, N.J.

[21] Appl. No.: 921,534

[22] Filed: Jul. 3, 1978

[51] Int. Cl.² .......................................... B65D 33/20
[52] U.S. Cl. ................................................. 206/363
[58] Field of Search ....................... 206/363, 439, 459; 229/80

[56] References Cited

U.S. PATENT DOCUMENTS

| | | | |
|---|---|---|---|
| 3,151,803 | 10/1964 | Kaminski | 229/80 |
| 3,819,106 | 6/1974 | Schuster | 206/439 |
| 3,920,870 | 11/1975 | Ackerman | 229/80 |
| 3,938,658 | 2/1976 | Rohde | 206/439 |
| 3,991,881 | 11/1976 | August | 206/439 |
| 4,121,714 | 10/1978 | Daly et al. | 206/363 |

*Primary Examiner*—Herbert F. Ross
*Attorney, Agent, or Firm*—Sprung, Felfe, Horn, Lynch & Kramer

[57] ABSTRACT

The sterilizable package and a method for packaging utilize a plastic member and a paper member marginally heat-sealed around all the sides thereof. A slit is provided in the paper extending between two side seals and adjacent to a space from another side seal for receiving the package contents. An adhesive layer is disposed around the paper member between the slit and the edge of the side adjacent to the slit for sealing the slit in response to a single fold along a bending line between the adhesive layer and the slit.

13 Claims, 4 Drawing Figures

STERILIZABLE PACKAGE AND A METHOD OF PACKAGING FOR STERILIZATION

BACKGROUND

The present invention relates to a sterilizable package and the method of packaging an article for sterilization, wherein the package is utilized which comprises a plastic member and a paper member which is marginally heat-sealed thereto.

Sterilizable packages or pouches made by marginally heat-sealing a clear plastic laminated surgical grade kraft paper or the like have come into widespread use. The paper portion of such packages is designed to be sufficiently porous to permit gas or steam sterilization, but is impervious to bacteria. The plastic laminate is heat-sealable to the paper, stable under sterilization conditions, impervious to bacteria and permit visual identification of the package contents.

Such packages are used for medical implements that must be sterilized prior to use. In one prior art type of package, as disclosed in U.S. Pat. No. 4,097,236, the manufacturer or user of such medical implements is supplied with a package which is heat-sealed around three sides by the package manufacturer. The medical implement is then placed in the package and the fourth side is heat-sealed to complete the marginal seal between the paper and the plastic.

After sterilization, either by exposure to ethylene oxide gas or by steam autoclaving, by the medical implement manufacturer or by the hospital or clinic which would use the medical implement, the package and its sterile contents can be stored for indefinite periods of time in a sterile condition.

While heat-sealing the fourth side of the package brings about the desired result that the package be completely sealed, it has been recognized that there is a need to be able to completely seal the package, after the insertion of the medical implement, without the need for special equipment.

While some solutions to this problem have been set forward, these have proven to be either unreliable or expensive to manufacture.

For example, packages are known wherein they can be closed by means of a single fold, such as in U.S. Pat. Nos. 3,070,280 and 3,811,613, however, neither of these packages seal same in the context of a seal which is reliable for sterilization.

Other packages, such as those disclosed in U.S. Pat. Nos. 3,254,828 and 3,298,580, 3,754,700 and 3,819,106 teach the use of complex constructions including overlying portions in order to close a package and seal it if necessary. Moreover, U.S. Pat. No. 3,942,713 teaches a package which can be closed and sealed as a result of a plurality of folds.

SUMMARY

The present invention provides a method and a sterilizable package which overcomes the problems heretofore encountered.

The method of the present invention for packaging an article for sterilization comprising providing a package having a plastic member and a paper member marginally heat-sealed around all sides thereof with a slit in the paper member extending between two side seals and adjacent to and spaced apart from another side seal an adhesive disposed between the slit and the edge of said another side. The article is inserted into the package through the slit and the package is folded only once around the bending line disposed between the adhesive and the slit to complete the sealing of the package.

The method also provides for a protective strip on the adhesive, wherein the protective strip is removed before folding.

The package of the present invention comprises a plastic member and a paper member marginally heat-sealed around all sides thereof, means defining a slit in the paper member extending between two side seals and adjacent to and spaced apart from another side seal for receiving the package contents and means disposed on the paper member between the slit and the edge of said another side for sealing the slit in response to a single fold at said another side of the package.

The sealing means preferably comprises an adhesive layer disposed at said another side and having a length greater than that of the slit and a width greater than that of the slit and means defining a bending line between the layer and the slit and around which the single fold is made to align the adhesive strip over the slit to completely envelope same.

In a preferred embodiment, the slit is parallel to the edge of said another side and extends completely between the two side seals, wherein the bend line is parallel to the slit and the adhesive layer extends along the whole length of the another side.

In the preferred embodiment the two side seals are perpendicular to the side opposite the slit and thereby perpendicular to the slit and the adhesive layer overlies a portion of the two side seals when the single fold is made.

A removable protective strip is also provided for overlying the adhesive layer and is removable before sealing the slit.

BRIEF DESCRIPTION OF THE DRAWINGS

The present invention will be more fully understood from the following description taken in conjunction with the accompanying drawings wherein.

DETAILED DESCRIPTION OF THE INVENTION

Figure 1:
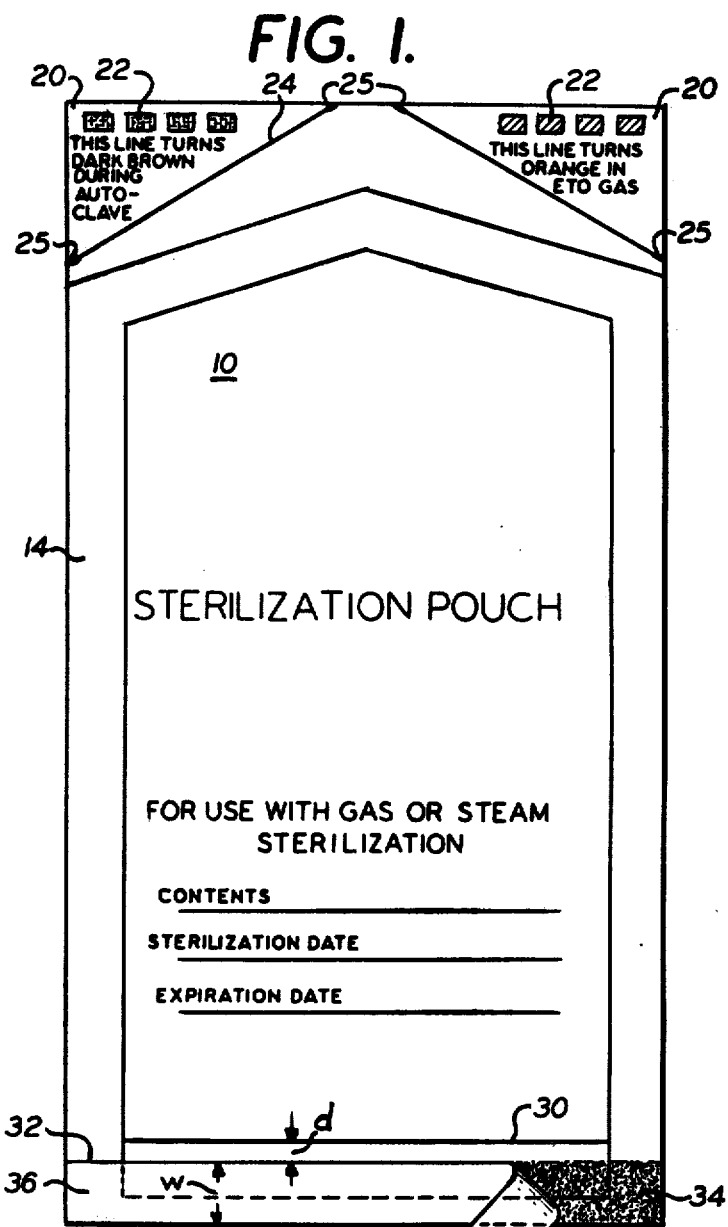
FIG. 1 is a top plan view of the sterilizable package according to the invention in its open state.
Figure 3:
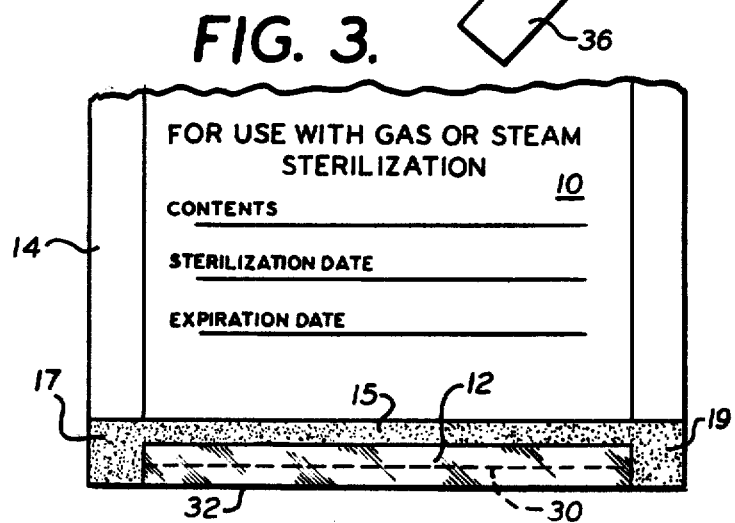
FIG. 3 is a top plan view of the package shown in FIG. 1 in its closed state.
Figure 2:
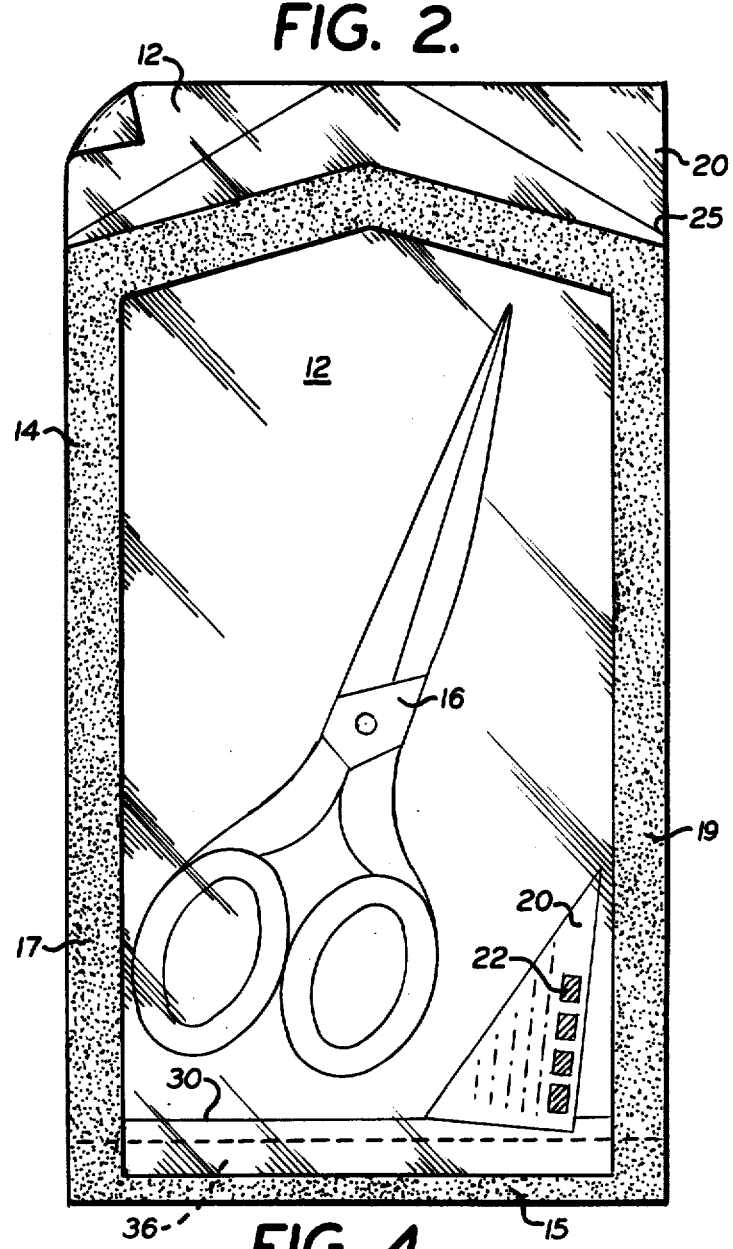
FIG. 2 is a bottom plan view of the package shown in FIG. 1.
Figure 4:
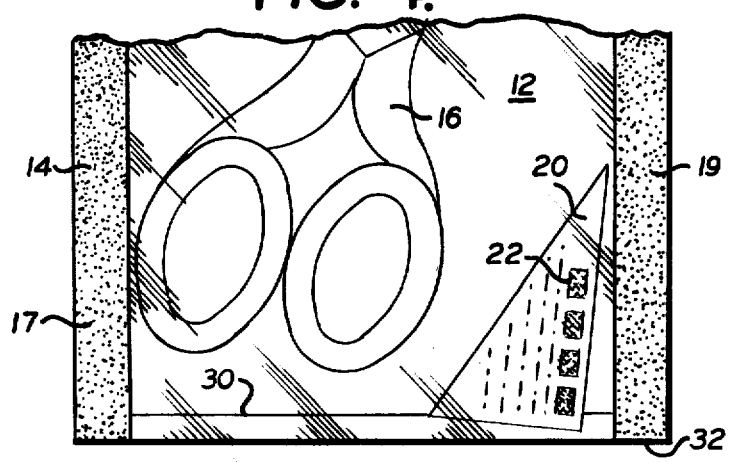
FIG. 4 is a bottom plan view of the package of FIG. 3.

Referring now to FIGS. 1-4, the sterilization pouch of the present invention includes a paper member 10 and a clear plastic laminate 12 which is marginally heat-sealed around all sides thereof by marginal heat seal 14. The chevron configuration at the top of the package is used to facilitate manual opening or peeling apart of the package to gain access to the package contents which is shown in FIGS. 2 and 4, for illustrative purposes, as a pair of scissors 16.

The term "paper" as used herein also applies to synthetic or artificial paper materials made from plastic fibers and the like, as well as conventional paper products having the necessary characteristics for use in sterilization pouches. An example of synthetic paper is a spun bounded polyethylene sold by duPont under the trademark "TYVEK".

The plastic member 12 is preferably a laminate of a polyester, such as polyethylene terephthalate sold under the trademark "MYLAR", and a heat-sealable thermoplastic material such as polyethylene, polypropylene, ethylene vinyl acetate, and ionomer such as duPont's "SURLYN", copolymers and mixtures of the foregoing. The polyester layer forms the exterior of the package and the heat-sealable thermoplastic material interfaces with the paper 10 and forms the marginal heat seal 14.

Heat-sealing the plastic member 12 to the paper 10 around the margin of the package as shown in FIGS. 1-4 can be accomplished using conventional heat-sealing equipment and techniques. Generally, the heat seal is made wide enough to guarantee an adequate and complete seal around the margin of the package. If desired, a number of parallel spaced apart seals can be effected in the area of the marginal seal 14. This is commonly known in the industry as a rib seal and is employed to impart additional peel strength to the heat seal between the plastic member 12 and the paper member 10. An example of this is shown in U.S. Pat. No. 4,091,921 wherein indicia for indicating sterilization conditions are utilized with this rib seal.

In order to insert the articles such as scissors 16 into the pouch for sterilization, slit 30 is provided in the paper. The slit extends between the two side seals 17 and 19, and while the length of the slit 30 may be less than the distance between the side seals 17 and 19, it is preferable that it extends the entire length between the side seals so as to preclude the tearing of the paper during the insertion of an article.

The slit 30 is positioned so as to be adjacent to side seal 15 which is between the two side seals 17 and 19 and spaced apart therefrom. In a particularly effective embodiment, where the side seal 15 is perpendicular to both the side seals 17 and 19, the slit 30 is parallel to side seal 15 and thereby perpendicular to both side seals 17 and 19.

Disposed on the paper member 10 is a layer or coating of adhesive disposed at the side seal 15 between the slit and the edge of the side corresponding to the side seal 15. The adhesive layer 34 has a length which is greater than that of the slit 30 and a width which is greater than that of slit 30 and in a particularly preferred embodiment, the adhesive layer 34 extends along the entire length of the paper member and overlies side seal 15 completely and a portion of side seals 17 and 19.

The adhesive may be either an adhesive coating deposited on the paper member, or an adhesive layer such as double sided adhesive tape which is laid down on the desired portion of the paper member as shown in FIG. 1. The adhesive may be any type of pressure sensitive or tacky adhesive which will stick to paper of the type hereinbefore mentioned and for example may be transfer tapes manufactured by 3M and others.

As shown in FIG. 1, a protective member 36 may be provided on the exposed face of the adhesive coating or layer 34 so as to prevent the interaction of the adhesive with any foreign objects prior to the sealing of the package. The protective member 36 overlies the adhesive layer and is preferably constructed as a strip which is removable as a result of the fact that it does not permanently interact with the adhesive 34. Any glossy material such as a plastic or a shiny finished wax paper may be used as the protective strip so long as it is removable by simple peeling.

In order to seal the contents of the package after the article 16 has been inserted through the slit 30, a bending line 32 is provided between the slit and the adhesive layer and around which a single fold is made to align the adhesive layer 34 over the slit 30 to completely envelope same. In order to define the bending line, the package may be pre-bent or indented. Alternatively, it has been found that the mere provision of the protective member 36 over the adhesive coating 34 defines the bending line due to the increased thickness thereof. Thus the inner edge of the protective member 36 provides a fulcrum about which the package can be pre-bent to define a bending line 32 and which, after the removal of the member 36 enables the package to be folded as shown in FIGS. 3 and 4 such that the slit is completely enveloped by the adhesive layer 34.

In order to effect a complete sealing of the slit 30, the distance d of the slit 30 from the bending line 32 should be greater than the distance from the inner edge of the adhesive to the bending line and less than the distance w of the outer edge of the adhesive member 34 to the bending line 32. In this way, when the single fold is made around the bending line 32, the adhesive layer 34 will completely surround the slit 30 and envelop same so as to seal the whole slit in a manner which is adequate for the sterilization of the pouch.

Furthermore, as discussed in detail in U.S. Pat. No. 4,097,236, the paper member 10 can be conveniently dyed or tinted a desired relatively dark color, for example dark blue, dark green, dark red, dark brown, dark grey, or black. Instead of dyeing or tinting the paper member 10, the paper member can have a relatively dark coating applied thereto, at least in the heat seal area. This can readily be accomplished by overprinting all or only the seal area of the paper member 10 with a dark ink such as the dark colors enumerated previously. That dye, tint or ink should be selected so as to be stable under sterilization conditions.

Readily available surgical grade kraft paper having the desired porosity characteristics can be readily dyed or overprinted to provide the desired relatively dark coloration for the paper member 10.

The plastic member 12 exhibits a relatively translucent appearance, which can be described as cloudly or milky as compared to the clear member itself, upon rupture or breaking of the heat seal area 14. This cloudy or milky appearance is believed to result from the heat sealing operation and only comes into being when the heat seal is ruptured or broken. This phenomenon is believed to result from a surface conformation by the plastic member 12 to the surface of the paper member 10. The paper member 10 usually has a dull or matte finish and this is duplicated in the seal area of the film in a cloudy or milky appearance upon rupture or breaking of the heat seal 14.

As a result, a visual contrast for readily detecting breaks or ruptures in the heat seal between the paper member 10 and the plastic member 12 is provided, whether due to partial opening of the package, either intentionally or unintentionally, or shifting of the package contents. It should also be noted that the sealed area 14 has a glossy, clear appearance which is in contrast to the dull or matte finish appearance of the paper member 10 through the plastic member 12 outside of the seal area 14. This contrast can be used to detect voids or defects in the heat seals made by the package manufacturer and also the packager.

Visual contrast also results when the package contents such as the pointed end of scissors 16 shifts and pierces or ruptures the heat seal 14. This results in a readily discernible translucent appearance which is in distinct color contrast with the dark coloration of the paper member 10 through the plastic member 12 in the unsealed areas of the package and is also in distinct color contrast with the remaining heat-sealed area 14 which shows the coloration of the paper member 10 in a clear and glossy fashion. Thus, in the case of a dark blue paper member, the user of a sterilized package can readily determine by a simple visual examination if the package, after sterilization, has been opened, either intentionally or unintentionally, that is, by peeling apart the two members 10 and 12 or whether the package contents, such as the scissors 16 has shifted and pierced or ruptured the heat seal 14. In either instance, the translucent portion which has a cloudy or milky appearance is in distinct color contrast with the dark coloration of the paper member 10 itself, which in this case is dark blue, and the remaining heat-sealed area which has a clear, dark blue coloration, but is glossy in appearance as compared to the matte or dull finish of the paper member 10 itself outside the seal area.

The same, highly visual color contrast results from imparting to the paper member 10 a relatively dark coloration such as dark blue, dark green, dark red, dark brown, dark grey, or black.

Referring also to FIGS. 1–4, the triangular shaped portions 20 extend beyond the inverted V-end seal which is beyond the area to be enclosed by the marginal heat seal 14. The paper 10 may have a white area or block printed thereon so that portions 20 can bear indicia that changes color upon sterilization, one portion bearing indicia that changes color upon steam sterilization and the other portion 20 indicia that changes color upon gas sterilization such as ethylene oxide gas. The indicia which is commonly referred to as indicator inks is generally shown by the reference numeral 22.

Suitable indicator inks for the indicia 22 are any of the commercially available and commonly used indicator inks for sterilization pouches. A typical indicator ink for use with steam autoclaving is a chemically active ink that changes from pink to dark brown during steam autoclaving. A typical indicator ink for use with ethylene oxide sterilization is a chemically active ink that changes color from light brown or tan to orange upon exposure to ethylene oxide gas sterilization.

Steam autoclaving and ethylene oxide gas are known sterilization techniques and the present invention is well adapted to these procedures.

An item to be sterilized such as the scissors 16 shown in FIG. 2 is inserted through the slit 30. Depending on the sterilization procedure to be employed, the technician separates the proper indicia bearing portion 20 each of which is attached to the paper portion 10 at 25 and precut therebetween along line 24. The technician or operator then inserts the separated portion 20 into the package with the indicia 22 visible through the plastic member 12 as shown in FIG. 2. The protective strip 36 is then removed, the package folded once bending line 32 and the seal is then completed and the package is ready for sterilization.

During sterilization, the sterilizing medium, steam or ethylene oxide gas, sterilizes the scissors 16 and at the same time or afterwards, reaches the indicia 22 which then undergoes the indicated color change to indicate that the package contents and not just the package itself are sterile. Depending on the nature and size of the item or implement to be sterilized, it is preferred to position the portion 20 which is inserted into the pouch between the item to be sterilized and the plastic member which ensures that the sterilization medium will not cause a color change in the color sensitive indicia until after the sterilizing medium has contacted the item to be sterilized. In any event, the indicia 20 must be visible through the plastic member 12 when the portion 20 is separated from the package and inserted into the interior thereof with the item to be sterilized.

The preferred embodiment shown in FIGS. 1 and 2 has a further advantage in that sealed packages ready for sterilization can be segregared by the intended sterilization procedure to be employed by virtue of the fact that one of the indicia-bearing portions 30 is missing from either the left or right side of each sealed pouch when the pouches are lined up and oreinted in the same direction. Thus, it is easy to detect if a package designated for steam sterilization has become mixed in with packages designated for ethylene oxide sterilization.

The sterilization pouch of the invention will typically bear other indicia, for example, on the exterior side of the paper member 12, preferably in a whitened area, to designate for example the package contents, the sterilization date, the expiration date and the like.

The color sensitive indicia 22 is commonly printed on the paper member 10 using known techniques.

What is claimed is:

1. A sterilizable package comprising a plastic member and a paper member marginally heat-sealed around all sides thereof; means defining a slit in the paper member extending between two side seals and adjacent to and spaced apart from another side seal for receiving the package contents; and means disposed on said paper member between the slit and the edge of said another side seal for closing the slit in response to a single fold of the package around a bending line between the slit and the edge of said another side seal of the package, said means being positioned such that upon making the single fold, said means is aligned over said slit.

2. The package according to claim 1, wherein the sealing means comprises an adhesive layer disposed at said another side and having a length greater than that of said slit and a width greater than that of the slit and means defining the bending line between the layer and the slit and around which said single fold is made to align the adhesive layer over the slit to completely envelop same.

3. The package according to claim 2, wherein the slit is parallel to the edge of said another side and extends completely between said two side seals, wherein the bend line is parallel to the slit and the adhesive layer extends along the whole length of said another side.

4. The package according to claim 3, wherein the two side seals are perpendicular to said another side and thereby perpendicular to the slit and the adhesive layer overlies a portion of the two side seals when the single fold is made.

5. The package according to claim 4 further comprising a removable protective strip overlying the adhesive layer and removable before sealing the slit.

6. The package according to claim 5, wherein the paper member comprises surgical grade kraft paper.

7. The package according to claim 6, wherein the plastic member comprises a laminate of a polyester and a heat-sealable thermoplastic material.

8. The package according to claim 7, wherein the adhesive comprises a pressure sensitive tape.

9. A sterilizable package according to claim 1, wherein the plastic member is clear and wherein a paper member is sufficiently porous to permit gas or steam sterilization but is impervious to bacteria and is dyed a dark color such that upon breaking the heat seal the previously clear plastic member takes on a translucent appearance in the area of the broken seal which provides a distinct color contrast between the break in the heat seal and the dark color of the paper in any remaining heat-sealed area.

10. A sterilizable package according to claim 1, wherein said paper member has a portion extending beyond the area to be enclosed by the marginal heat seal, said portion bearing indicia that changes color upon sterilization and means releasably joining said portion from the remainder of the paper member to enable separation for insertion together with the package contents into the package prior to sealing the slit and sterilization of the package contents to indicate that the package contents have been subjected to sterilization.

11. Package of claim 10, wherein said portion extending beyond the area enclosed by the heat seal has two parts, one part bearing indicia that changes color upon steam sterilization and the other part bearing indicia that changes color upon gas sterilization and wherein the releasable joining means includes means enabling the individual separation of each part from the package, to signify on its face to a user that the package is to be subjected to steam sterilization if the one part is removed and to gas sterilization if the other part is removed.

12. Package of claim 10, wherein the heat seal includes an inverted end V-seal joining two side seals and the indicia bearing portion of the paper member extending beyond the inverted V-seal is at least one triangular-shaped member.

13. Package of claim 12, wherein two triangular members are provided, one member bearing indicia that changes color upon steam sterilization and the other member indicia that changes color upon gas sterilization and wherein the releasable joining means includes means enabling individual separation of each triangular member from the package to signify on its face to a user that the package is to be subjected to steam sterilization if the one member is removed and to gas sterilization if the other member is removed.

* * * * *